(12) United States Patent
Brandt et al.

(10) Patent No.: US 10,092,437 B2
(45) Date of Patent: Oct. 9, 2018

(54) FOREARM AND WRIST SUPPORT SLEEVE

(71) Applicant: NIKE, Inc., Beaverton, OR (US)

(72) Inventors: Baron C. Brandt, Portland, OR (US);
Iustinia Koshkaroff, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 268 days.

(21) Appl. No.: 14/936,380

(22) Filed: Nov. 9, 2015

(65) Prior Publication Data
US 2016/0128859 A1     May 12, 2016

Related U.S. Application Data

(60) Provisional application No. 62/077,700, filed on Nov. 10, 2014.

(51) Int. Cl.
| | |
|---|---|
| *A63B 71/12* | (2006.01) |
| *A61F 5/01* | (2006.01) |
| *A61F 5/058* | (2006.01) |
| *A41D 13/08* | (2006.01) |
| *A41D 19/00* | (2006.01) |

(52) U.S. Cl.
CPC ............ *A61F 5/0118* (2013.01); *A41D 13/08* (2013.01); *A41D 19/0044* (2013.01); *A61F 5/05858* (2013.01); *A41D 2400/10* (2013.01); *A63B 71/12* (2013.01); *A63B 2209/10* (2013.01); *A63B 2225/09* (2013.01)

(58) Field of Classification Search
CPC ... A61F 5/0118; A61F 5/05858; A41D 13/08; A41D 19/0044; A41D 2400/10; A63B 71/12; A63B 2225/09; A63B 2209/10

USPC ............................................................ 602/63
See application file for complete search history.

(56) References Cited

U.S. PATENT DOCUMENTS

| | | | |
|---|---|---|---|
| 1,517,984 A | 12/1924 | Harvey | |
| 1,851,011 A | 3/1932 | Jensen | |
| 2,832,074 A | 4/1958 | Wheeler | |
| 5,817,038 A * | 10/1998 | Orange | A61F 13/041 602/3 |
| 6,155,084 A * | 12/2000 | Andrews | A41D 13/08 2/16 |
| 6,523,180 B1 * | 2/2003 | Christopher | A01K 15/02 119/714 |
| 9,901,130 B2 * | 2/2018 | Morris | A63B 71/145 |
| 2003/0060845 A1 * | 3/2003 | Gardon-Mollard | A61F 13/085 606/201 |
| 2007/0204373 A1 * | 9/2007 | Loyens | A41D 13/08 2/16 |

OTHER PUBLICATIONS

International Preliminary Report on Patentability dated May 26, 2017 for International Patent Application No. PCT/US2015/059936, 8 pages.

(Continued)

*Primary Examiner* — Tarla Patel
(74) *Attorney, Agent, or Firm* — Shook, Hardy & Bacon LLP (57) ABSTRACT

A wrist and forearm sleeve is adjustable to provide varying amounts of compression and support at different positions along the wrist and forearm. Among other things, the sleeve might include an elastic internal sleeve, an adjustable cuff, and an adjustable sheath. In addition, a method of supporting a wrist and forearm includes donning the wrist and forearm sleeve.

14 Claims, 7 Drawing Sheets

(56) References Cited

OTHER PUBLICATIONS

International Search Report with Written Opinion dated Mar. 3, 2016 in Application No. PCT/US2015/059936, 12 pages.

* cited by examiner

FOREARM AND WRIST SUPPORT SLEEVE

CROSS REFERENCE TO RELATED APPLICATIONS

This application claims priority to U.S. Provisional Application No. 62/077,700 (filed on Nov. 10, 2014), which is incorporated herein by reference in its entirety.

TECHNICAL FIELD

This application is related to sleeves for supporting a wrist and a forearm during various activities, such as track-and-field events.

BACKGROUND

In various activities, a person may benefit from a device that supports his or her wrist and forearm. However, the operation of the device (e.g., size, amount of compression, adjustability) may depend on different variables, such as the anatomy of the person and the activity in which he or she is engaging.

BRIEF SUMMARY

In brief, and at a high level, an aspect of the present invention is directed to a wrist and forearm sleeve that is adjustable to provide varying amounts of compression at different positions along the wrist and forearm. Among other things, the sleeve might include an elastic internal sleeve, an adjustable cuff, and an adjustable sheath.

Aspects of the invention are defined by the claims below, not this summary. A high-level overview of various aspects is provided here to introduce a selection of concepts that are further described in the detailed-description section below. This summary is not intended to identify key features or essential features of the claimed subject matter, nor is it intended to be used as an aid in isolation to determine the scope of the claimed subject matter.

BRIEF DESCRIPTION OF THE DRAWINGS

The present invention is described in detail herein with reference to the attached drawing figures, which are incorporated herein by reference in their entirety, wherein.

DETAILED DESCRIPTION

The subject matter of aspects of the present invention is described with specificity herein to meet statutory requirements. But the description itself is not intended to necessarily limit the scope of claims. Rather, the claimed subject matter might be embodied or carried out in other ways to include different elements or combinations of elements similar to the ones described in this document, in conjunction with other present or future technologies.

Aspects hereof provide a wrist and forearm sleeve that can be worn by a person when engaging in various activities. Among other things, the sleeve may provide support and/or compression to the person's wrist and forearm. Generally, the sleeve may be slid over a person's wrist and forearm and adjusted to control an amount of support and/or compression provided. In addition, the sleeve may be re-adjusted throughout the course of an activity, or as the person transitions to a different activities, should the person desire to modify the amount of support or compression provided by the sleeve. Among other things, the sleeve might include a tubular body that is at least partially elastic and that is coupled to an adjustable cuff and/or an adjustable outer sheath. In one aspect, the internal sleeve provides a first amount of compression, which is adjustable at various positions using the cuff and/or the adjustable outer sheath.

Figure 1:
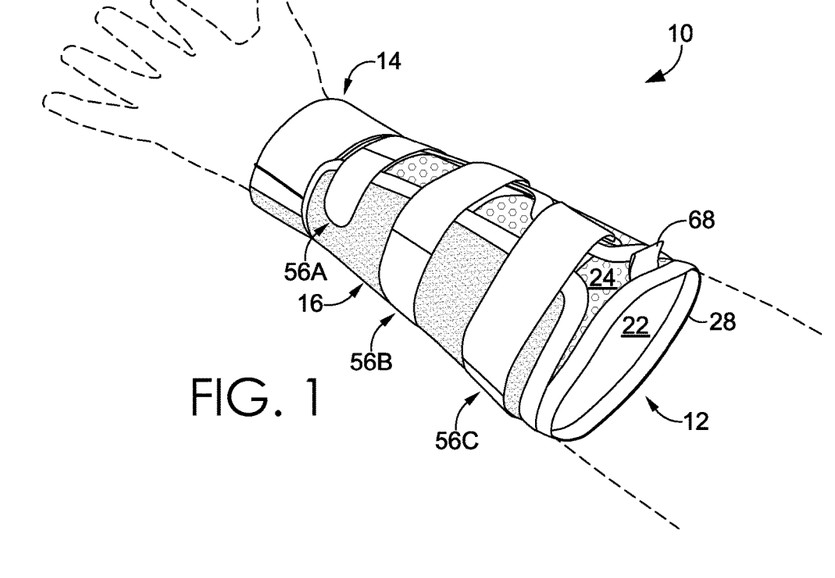
FIG. 1 depicts a first version of a sleeve in accordance with an aspect hereof.
Figure 2:
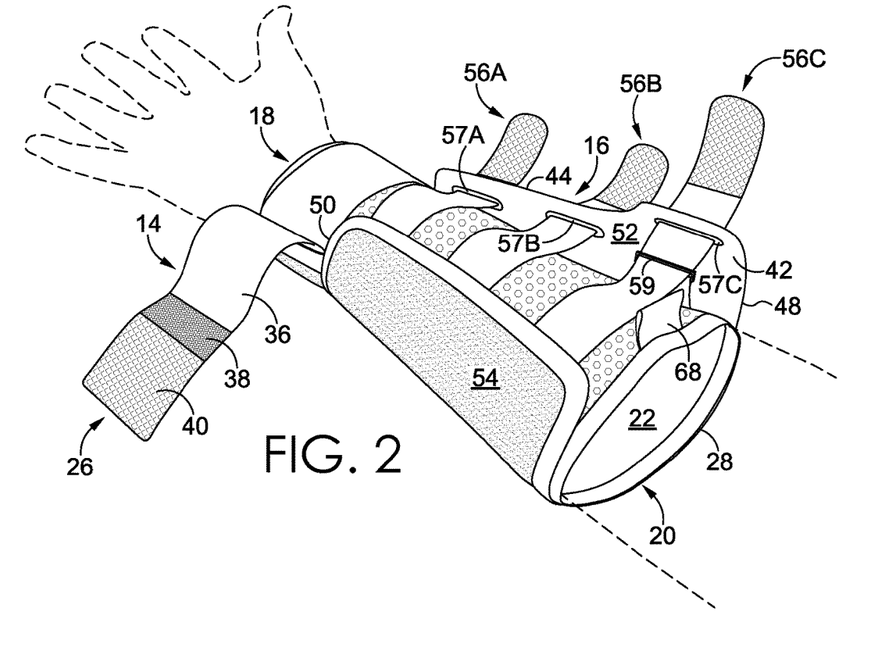
FIG. 2 depicts the sleeve of FIG. 1 with releasable fasteners at least partially detached in accordance with an aspect hereof.

Referring now to FIGS. 1 and 2, an exemplary sleeve 10 is depicted. FIG. 1 depicts the wrist cuff and forearm straps in a coupled state, such as when the sleeve is tightened onto a wearer's arm, and FIG. 2 depicts the wrist cuff and forearm straps decoupled, such as when the sleeve 10 is being pulled on or is being adjusted. Generally, the sleeve includes a tubular body 12 that is at least partially elastic and that is slidable over a person's hand and onto his or her wrist and forearm, which are shown in a ghosted view for illustrative purposes. The sleeve also includes a cuff 14 and a sheath 16 that are both adjustable at one or more positions along the tubular body 12 to provide a selected amount of compression to the wearer's wrist and/or forearm. For example, the sheath might be independently adjusted at different zones along the sleeve 10 using straps 56A, 56B, and 56C.

Figure 4:
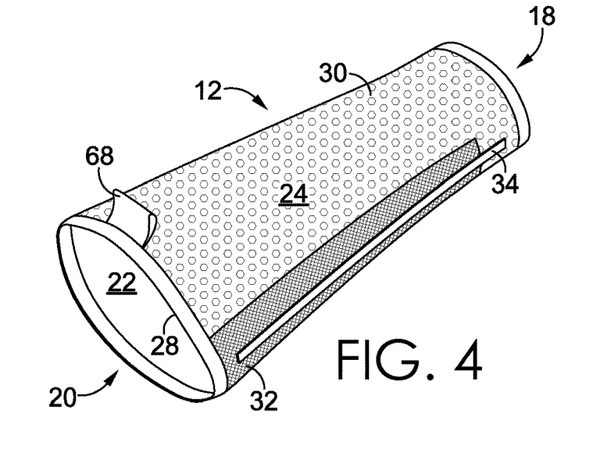
FIG. 4 depicts an elastic tubular body in accordance with an aspect hereof.

Having described some general aspects of the sleeve 10, the tubular body 12 will now be described in greater detail with reference to FIG. 4. In FIGS. 1 and 2, the tubular body 12 is partially obstructed from view by other portions of the sleeve 10. So in order to better illustrate the tubular body 12, FIG. 4 provides an illustrative view in which the tubular body is depicted separately from some of the other exemplary parts of the sleeve 10. For example, FIG. 4 depicts the tubular body 12 detached from the cuff 14 and the sheath 16. Although the tubular body 12 is illustrated as detached for explanatory purposes, in other aspects, the tubular body 12 might be secured to the cuff 14 and/or sheath 16 by a fastening means (e.g., adhesive, weld, stitch, etc.) that is not meant to be releasably detachable.

The tubular body 12 includes a first end 18 and a second end 20. For explanatory purposes, the first end 18 and the second end 20 might be described in terms that relate to the wearer or to other parts of the sleeve 10 and that are relative to one another. For example, the first end 18 might be referred to as the "wrist end" because the first end 18 is generally closer to a wrist of the wearer than is the second end 20 when the sleeve 10 is donned in the manner depicted in FIGS. 1 and 2. The first end 18 may also be referred to as the "cuff end" because the first end 18 is generally closer to the cuff 14 of the sleeve than to the sheath 16. In other aspects, the first end 18 may be referred to as the "distal end" because it may generally be relatively further away from the main body when measured along the extremity (as compared with the second end 20) when the sleeve 10 is donned in the manner depicted in FIGS. 1 and 2. The second end 20 might also be similarly described using relative descriptors, such as the forearm end, sheath end, or proximate end. That is, the second end 20 might be referred to as the "forearm end" because the second end 20 is generally closer to a forearm of the wearer than is the first end 18 when the sleeve 10 is donned in the manner depicted in FIGS. 1 and 2. The second end 20 may also be referred to as the "sheath end" because the second end 20 is generally closer to the sheath 16 of the sleeve than to the cuff 14. In other aspects, the second end 20 may be referred to as the "proximal end" because it may generally be relatively closer to the main body when measured along the extremity (as compared with the first end 18) when the sleeve 10 is donned in the manner depicted in FIGS. 1 and 2.

The tubular body 12 also includes a tubular wall 28 that is constructed of one or more segments having respective textile elements. For example, in FIG. 4, the tubular body 12 includes a first segment 30 having a first textile element and a second segment 32 having a second textile element. The textile elements 30 and 32 might have different properties, such as elasticity, breathability, and rigidity and might be constructed into the wall 28 at a respective strategic position to provide certain functionalities. For example, the first textile element 30 might have a higher elasticity than the second textile element 32 and might be constructed into the wall 28 to provide more elasticity to a targeted forearm region (e.g., ventral side). The second textile element 32 might be constructed into the wall to provide less elasticity at other regions, such as along the ulna.

Figure 13:
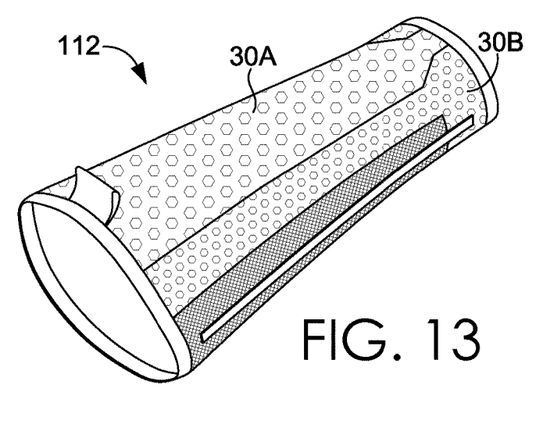
FIG. 13 depicts another elastic tubular body in accordance with an aspect hereof.

As depicted in FIG. 4, the wall 28 includes a segment of the first textile element 30 that extends continuously from the first end 18 to the second end. But in other aspects, the segment 30 might extend only partway from the first end 18 towards the second end 20 or only partway from the second end 20 towards the first end 18. For example, FIG. 4 illustratively depicts the second segment 32 (less elastic than 30) extending only partway from the second end 20 towards the first end 18. But in other aspects, the second-textile segment 32 might extend contiguously from the second end 20 to the first end 18. In addition, although FIG. 4 depicts each segment 30 and 32 as a single piece of textile, each of these segments might be constructed of multiple segments that are affixed together in a patchwork fashion. For example, FIG. 13 depicts an alternative tubular body 112 having segments 30A and 30B that are affixed together. Among other things, using multiple segments in this manner allows a contour of the tubular body 112 to be constructed to fit on a forearm and wrist. In addition, each of these segments might include multiple layers of textile.

In addition, the tubular body 12 includes an inward-facing surface 22 and an outward-facing surface 24. The inward-facing surface 22 faces towards a space that is at least partially enclosed by the tubular body 12 and that receives a wrist and/or forearm when the sleeve 10 is worn, and the outward-facing surface 24 faces away from the space. The inward-facing surface 22 may provide include various features that contribute to the functionality of the sleeve 10. For example, the inward-facing surface 22 might include a comfort-enhanced surface to enhance the comfort of the sleeve 10. The outward-facing surface 24 faces away from the space and interfaces with other parts of the sleeve 10, such as the cuff and the sheath. In addition, other components might be affixed against the outward-facing surface 24. For instance, if the cuff 14 is affixed to the tubular body 12, then the cuff 14 may be affixed against the outward-facing surface 24.

In a further aspect, the tubular body 12 includes a stiffening rib or tubing 34 that is coupled to the wall 28. The rib 34 includes one or more elongated members that are generally more rigid than the wall 28. The rib 34 might be coupled to the tubular body 12 in various manners. For example, the rib 34 may be coupled directly to the outward-facing surface 24, such as depicted in FIG. 4. Alternatively, a rib might be coupled against the inward-facing surface 22 or between layers of the wall 28. The rib 34 might be positioned on the wall 28 to provide desired rigidity to a region that corresponds with a particular part of the wearer's anatomy, such as the ulna. In addition, the rib 34 might combine with the segment 32, which is less elastic than the segment 30, to provide a region of the wall that is both less elastic and more rigid. Although only a single rib 34 is depicted in FIG. 4, the tubular body 12 might be constructed to include a plurality of ribs in various positions around the tubular body 12.

In a further aspect, the tubular body 12 includes a pull tab 68 that is fixedly attached near the second end 20 and that includes a strip or loop for pulling the tubular body 12 onto a wearer's arm. The pull tab 68 might include various structures such as a loop of textile, a chord loop, a webbing loop, or a variety other structures that could be gripped in order to improve one's ability to pull the tubular body 12. In one aspect, the pull tab 68 is less elastic than the portion of the tubular body 12 to which the pull tab is attached.

As previously indicated, the cuff 14 may be attached directly to the tubular body 12. Referring to FIG. 2, the sleeve 10 includes the cuff 14 that is attached near the first end 18 of the tubular body 12 and to the outward-facing surface 24. Generally, the cuff 14 includes a strip of one or more textile elements having an attachment end and a releasably-attachable end 26. The attachment end of the cuff 14 is fixed to the outward facing surface 24, such as by stitching, adhering, welding, and the like. The releasably-attachable end 26 releasably attaches to at least another portion of the strip and/or to the outward-facing surface, using a releasable fastener, such as hook-and-loop components, snaps, clips, buckles, and the like.

In one aspect, the one or more textile elements of the cuff 14 include segments having different properties. For example, in FIG. 2 (and FIG. 5), the cuff 14 includes a first cuff segment 36 that is proximate to the attachment end of the cuff 14 and another cuff segment 38 that is adjacent to the first cuff segment 36. In addition, the cuff 14 includes a releasably-fastened segment 40, which releasably fastens onto another portion of the cuff 14 or sleeve 10.

Figure 5:
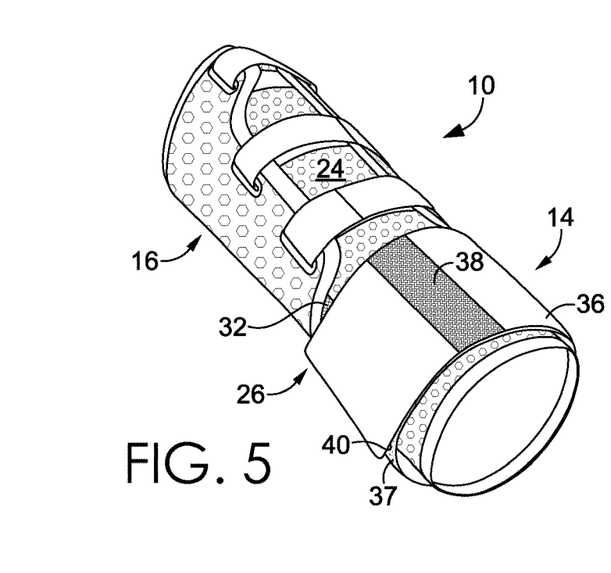
FIGS. 5-9 depict other views of the sleeve in FIG. 1 in accordance with aspects hereof.

In one aspect, the cuff segments 36 and 38 have different amounts of elasticity, which combine to provide a desired amount of wrist support and adjustable compression. For example, the cuff segment 38 might be more elastic than the cuff segment 36 to enable the cuff 14 to stretch when being tightened. The cuff segments 36 and 38 might have other different respective qualities as well, such as stiffness, rigidity, pliability, breathability, and the like. To achieve different qualities and functionality among the segments 36 and 38 different textiles might be used. For instance, in one aspect one or more of the segments 36 and 38 might include suede, which can help to impede the cuff 14 from shifting. The segments 36 and 38 may also include various woven, non-woven, and/or knitted textile, or other synthetic materials.

In a further aspect, a portion 37 of the segment 36 might include part of a releasable fastener that mates with the releasably-fastened segment 40. For example, FIG. 2 depicts that the segment 40 includes a first part of hook-and-loop fastening system that mates with a second part 37 of a hook-and-loop fastening system depicted in FIG. 7. In addition, other types of releasable fasteners might be used, such as a buckle system, clip, snap, and the like.

Figure 3:
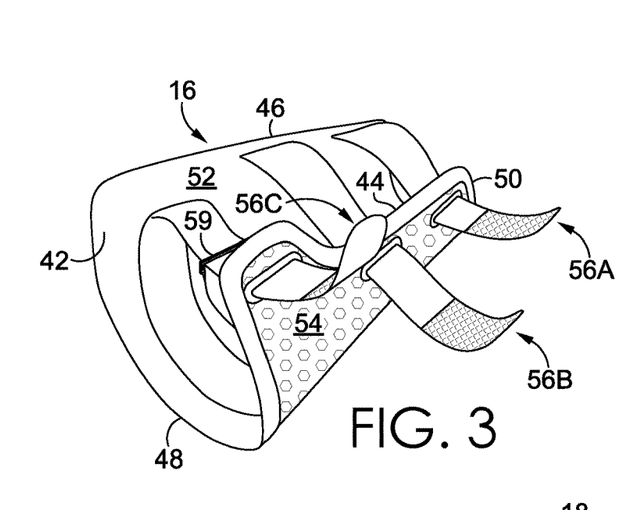
FIG. 3 depicts a first version of a sheath in accordance with an aspect hereof.

As previously mentioned, the sleeve 10 includes the adjustable forearm sheath 16 that at least partially encases the tubular body 12 and that adjustably fastens around the tubular body 12 to adjust a size of the sleeve 10 and an amount of compression and support provided by the sleeve 10. Because some portions of the sheath 16 may be obscured from view in FIGS. 1 and 2, another view is depicted in FIG. 3 in which the sheath 16 is shown detached from the tubular body 12. However, in other aspects the sheath 16 and tubular body 12 might be connected in a manner that is not intended to be detached, such as by stitching, welding, adhering, and the like.

At a high level, the sheath 16 includes a sheet of textile 42 that is adjustable around the tubular body 12. In one aspect the sheet of textile 42 is relatively non-elastic as compared with the tubular body 12. That is, the tubular body 12 includes a segment 30, which is relatively elastic and stretches to provide substantially evenly distributed compression across a broad region of the forearm. On the other hand, the sheet of textile 42 is relatively non-elastic and is more rigid than the segment in order to provide support to the wearer. The sheath 16 includes an adjustable mechanism (e.g., adjustable straps or cables) that allows the sheath 16 to be tightened in specific regions.

In one aspect, the sheet of textile 42 is defined by at least a first edge 48, a second edge 50, a third edge 44, and a fourth edge 46. In addition, the sheath includes an internal-facing surface 52 and an external surface 54. Referring to FIG. 2, the first edge 48 and the second edge 50 extend radially around the elastic tubular body, the first edge 48 being positioned near the second end 20 of the tubular body 12 and the second end 50 being positioned near the cuff 14. In addition, the third edge 44 and the fourth edge 46 extend axially relative to the tubular body 12 and that couple the first edge to the second edge. "Axially" refers to being in-line with an axis that extends lengthwise through the space partially enclosed by the tubular body.

In a further aspect the sheath 16 includes an adjustable attachment mechanism that releasably attaches at different positions to the external surface 54 of the sheath to adjust the size of the forearm sleeve 10 and amount of support and compression provided by the sleeve. For example, in FIGS. 2 and 3 the adjustable attachment mechanism includes a set of hook-and-loop strips 56A, 56B, and 56C that extend through apertures or eyelets 57A, 57B, and 57C near the third edge 44 and that can be mated with a corresponding part of a hook-and-loop fastening system on the external surface 54 of the sheath. In FIG. 3, strips 56A and 56B are anchored to the internal surface 52 of the sheath 16 such that fastening the strips 56A and 56B to the external surface 54 pulls the fourth edge 46 towards the third edge 44. In addition, strip 56C is anchored to itself by another eyelet 59 (e.g., rectangular loop ring or buckle), such that by tightening strip 56C a user has more acute control over an amount of compression that is provided.

Figure 6:
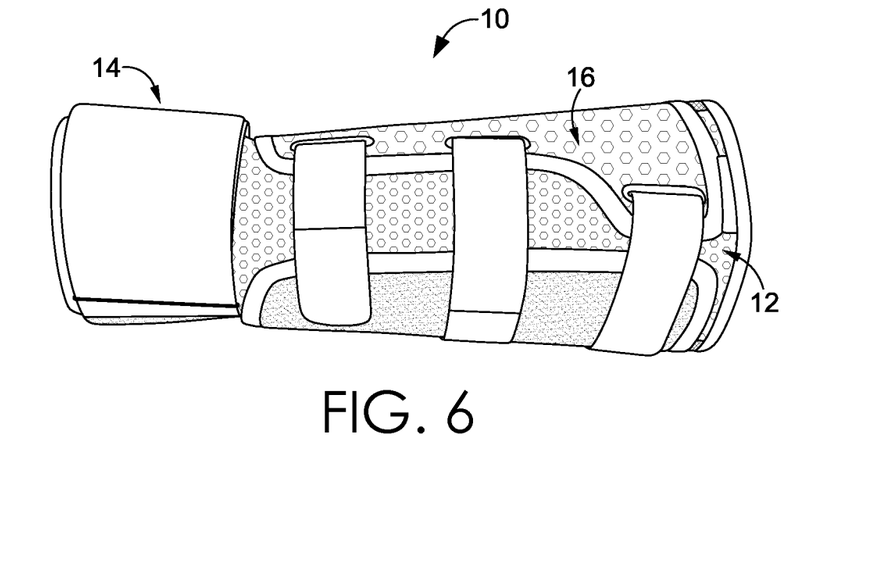
Figure 7:
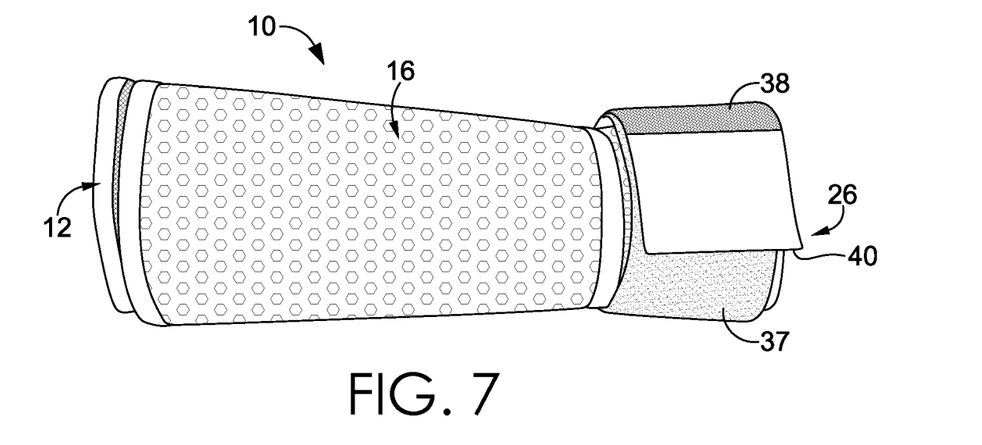
Figure 8:
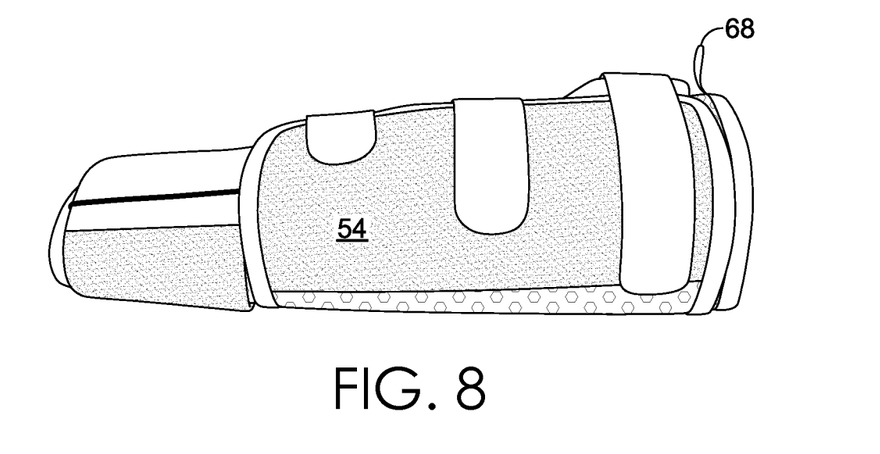
Figure 9:
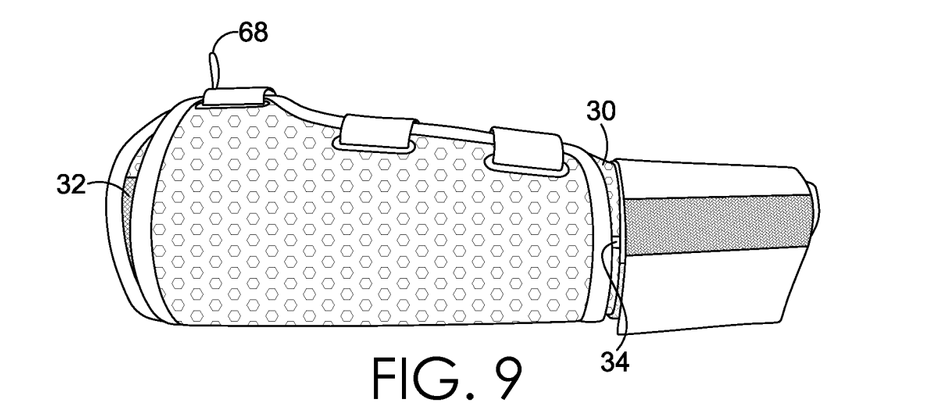

FIGS. 5-9 depict other views of the sleeve 10 that is depicted in FIGS. 1-4. For example, FIG. 5 depicts a wrist-end isometric perspective. Among other things, FIG. 5 illustrates that the less-elastic segment 32 might align on a side of the sleeve 10 and that the attachment end 40 of the cuff 14 attaches onto the mating surface 37. FIG. 6 depicts a plan view of the ventral-aligned side of the sleeve 10, and FIG. 7 depicts a dorsal-aligned side of the sleeve. FIG. 8 depicts a left side of the sleeve and FIG. 9 depicts a right side of the sleeve.

Figure 10:
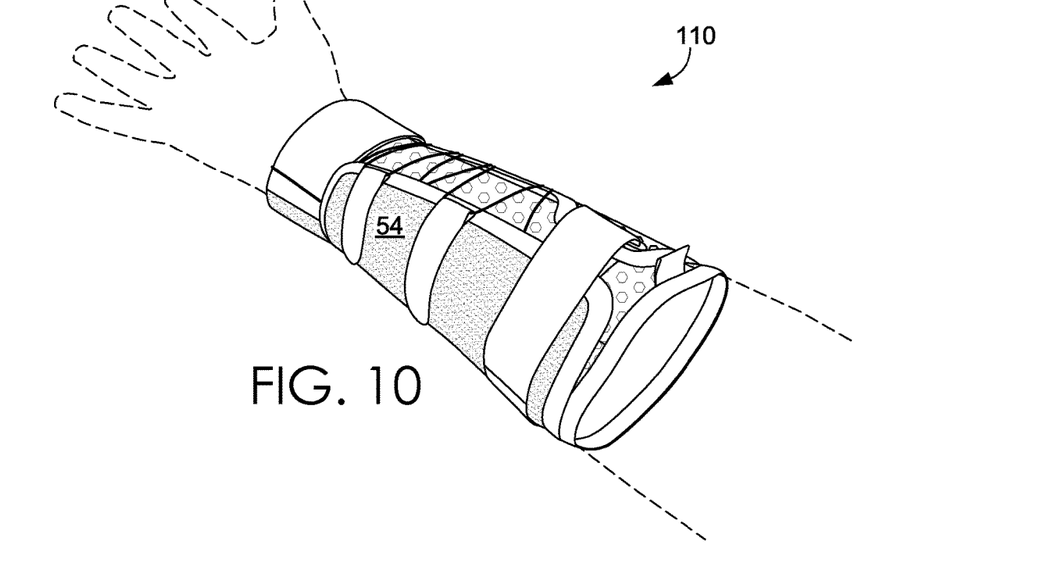
FIG. 10 depicts another version of a sleeve in accordance with an aspect hereof.
Figure 11:
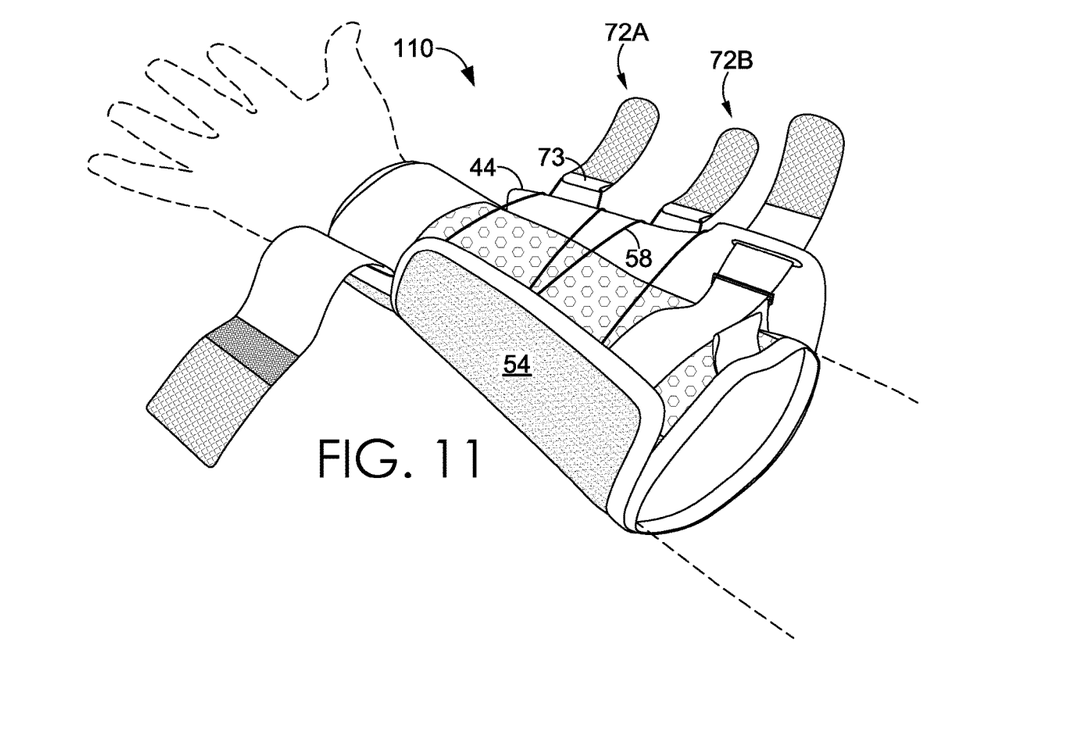
FIG. 11 depicts the sleeve of FIG. 10 with releasable fasteners at least partially detached in accordance with an aspect hereof.
Figure 12:
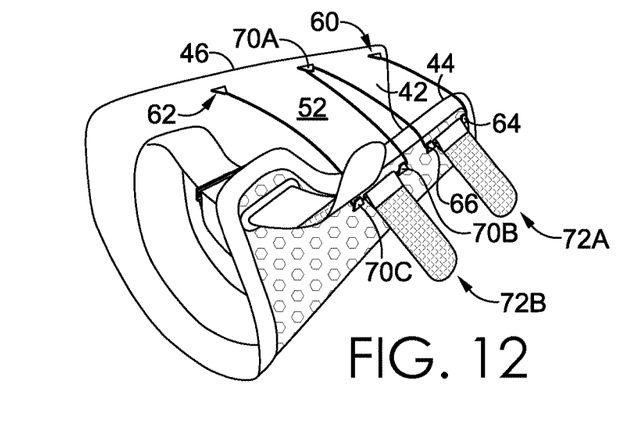
FIG. 12 depicts another version of a sheath in accordance with an aspect hereof.

In other aspects of the present technology, a wrist and forearm sleeve might include an adjustable mechanism that is different from the particular strap arrangement depicted in FIGS. 1-9. Referring to FIGS. 10-11 a sleeve 110 is depicted that includes another type of adjustable attachment mechanism, which is shown in greater detail in FIGS. 11 and 12. The mechanism depicted in FIGS. 10-16 may be used instead of, or in addition to, the straps 56A and 56B that are depicted in FIGS. 1-9. In one aspect, the adjustable attachment mechanism includes a cable 58 that is attached at a first end 60 to the sheath body 42. For example, the cable 58 might be secured to the inside surface 52 near the fourth edge 46, as depicted in FIG. 12. In addition, the cable 58 slidably extends through a first eyelet or fabric loop 64 near the third edge 44, as well as a second eyelet or fabric loop 66 near the third edge 44. The cable 58 is also attached to the sheath body 42 at a second cable end 62.

In a further aspect, the adjustable attachment mechanism includes at least one hook-and-loop strip 72A that is slidably attached to the cable 58 along a portion of the cable extending between the first eyelet 64 and the second eyelet 66. For example, the hook-and-loop strip 72A includes a cable sleeve 73 constructed into one end that allows for slidable attachment to the cable 58. The hook-and-loop strip 72A mates with a corresponding hook-and-loop mechanism that is on the outside surface 54, as depicted in FIG. 10.

In a further aspect, the cable 58 might pass through a series of other eyelets or fabric loops 70A, 70B, and 70C, and might include one or more additional hook-and-loop mechanisms 72B, each of which provides additional compression and support to a targeted area of the sleeve. Although the ends of the cable 58 are shown as being attached near the fourth edge 46, in another aspect, one or both ends are attached near the third edge 44.

Figure 14:
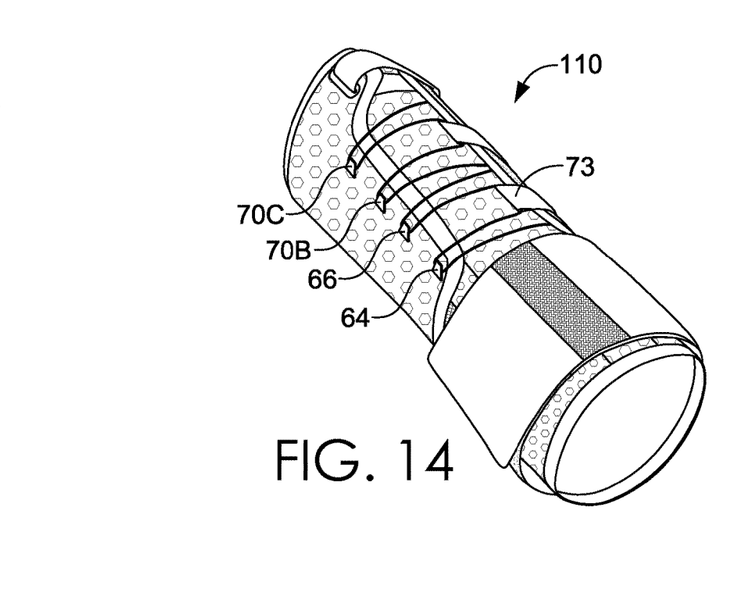
FIGS. 14-16 depict other views of the sleeve in FIG. 10 in accordance with aspects hereof.
Figure 15:
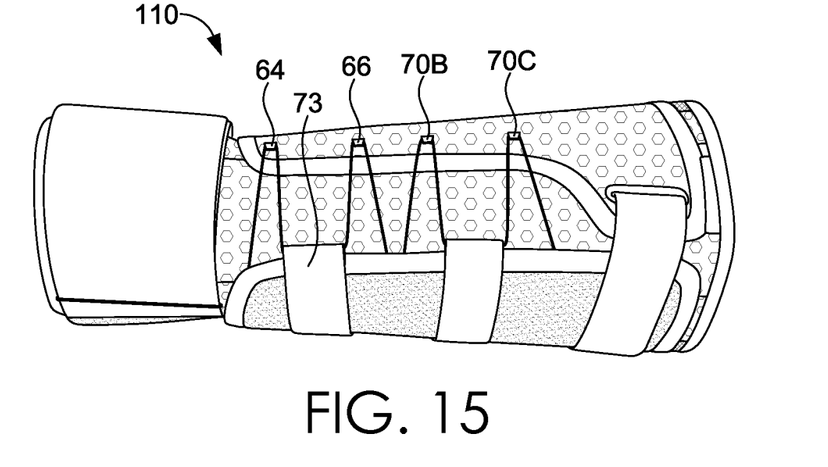
Figure 16:
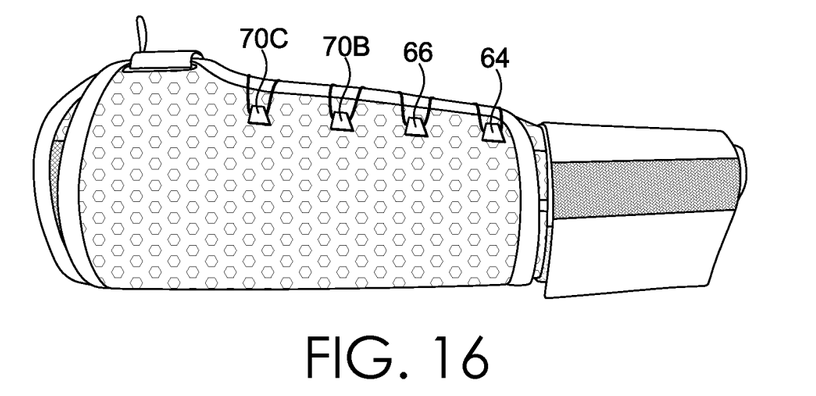

FIGS. 14-16 depict other views of the sleeve 110 depicted in FIGS. 10-13. FIG. 14 depicts a wrist-end isometric perspective, and FIG. 15 depicts a plan view of the ventral-aligned side. Among other things, FIGS. 14 and 15 show how the cable tightening system might be attached to hold the sleeve in a configuration that provides compression and support. FIG. 16 depicts a right side of the sleeve, showing the cable-system attachment points 64, 66, 70B, and 70C.

Although the figures depict exemplary sleeves that include an illustrated number of straps 56A-C or other adjustment mechanism 72A and 72B, in other aspects a sleeve might include fewer or more straps or adjustment mechanisms. For example, a sleeve might include a wrist strap and one or two forearm adjustment straps. Alternatively, a sleeve may include a wrist strap and four or more adjustment straps.

The technology may include various other aspects, and in describing these other aspects, reference will be made to one or more of the previously described figures for illustrative purposes. One exemplary aspect includes forearm sleeve (e.g., FIGS. 1-9, element 10 or FIGS. 10-16, element 110) that includes an elastic tubular body (e.g., 12 or 112), a cuff (e.g., 14), and an adjustable forearm sheath (e.g., FIG. 3 or FIG. 12). Generally, the elastic tubular body includes a first end (e.g., 18) and a second end (e.g., 20) and includes an inward-facing surface (e.g., 22) and an outward-facing surface (e.g., 24). In addition, the cuff is generally attached near the first end and to the outward-facing surface. The cuff includes a strip of one or more textile elements that includes an attachment end attached to the outward-facing surface and a releasably-attachable end (e.g., 26) that releasably attaches to at least one of another portion of the strip and the outward-facing surface. In a further aspect, the adjustable forearm sheath that at least partially encases the elastic tubular body near the second end and that adjustably fastens around the elastic tubular body to adjust a size of the forearm sleeve.

In a further aspect, the elastic tubular body (e.g., 12 or 112) includes a tubular wall (e.g., 28) comprised of a plurality of textile pieces (e.g., 30 and 32 or 30A/B and 32) coupled to one another. For instance, the plurality of textile pieces may include at least a first type of material (e.g., 30) and a second type of material (e.g., 32), and the first type of material may have an elasticity that is greater than the second type of material. In addition, the elastic tubular body may include a first tubular segment that extends from the first end to a central region between the first end and the second end, the first tubular segment including a material having an amount of elasticity greater than the second type of material. For example, in FIGS. 4 and 13 a tubular portion of the elastic tubular body is positioned between the segment 32 and the first end 18, the segment possibly being aligned with a wrist of the wearer when the sleeve is worn. Further, the elastic tubular body may include a second tubular segment that extends from the second end to a central region between the second end and the first end, at least a portion of the second tubular segment including the second type of material (e.g., 32) having the lower amount of elasticity. In another aspect, an elongated rib element (e.g., 34) may axially extend along the elastic tubular body. In addition, the elastic tubular body may include a pull tab (e.g., 68) that is fixedly coupled to the second end and that includes an amount of elasticity that is less than the elastic tubular body.

In a further aspect of the forearm sleeve, the strip of one or more textile elements (i.e., of the cuff) includes a first strip segment comprised of a first type of material (e.g., 36) and a second strip segment comprised of a second type of material (e.g., 38), the first type of material having a lower elasticity than the second type of material. In addition, the first strip segment may extend from the attachment point (i.e., of the strip to the elastic tubular body) to a central portion of the strip positioned between the attachment end and the releasably-attachable end. In addition, the second strip segment may extend from the first strip segment at the central portion of the strip to a hook-and-loop-fastener segment (e.g., 40) at the releasably-attachable end.

In another aspect of the forearm sleeve, the adjustable forearm sheath includes a sheet of textile (e.g., 42) that is less elastic than the elastic tubular body. In an exemplary instance, the sheet of textile includes a first edge (e.g., 48) and a second edge (e.g., 50) that extend radially around the elastic tubular body, the first edge being positioned near the second end of the elastic tubular body and the second end positioned near the cuff. In addition, the sheet of textile material may include a third edge (e.g., 44) and a fourth edge (e.g., 46) that extend axially relative to the elastic tubular body and that couple the first edge to the second edge. As such, the first, second, third, and fourth edges may form a perimeter boundary of a sheath body, which includes an internal surface (e.g. 52) facing towards the elastic tubular body and an external surface (e.g. 54). However, the sheet of textile may include more edges or fewer edges that form a perimeter boundary. In a further aspect, the adjustable forearm sheath includes an adjustable attachment mechanism that releasably attaches at different positions to the external surface to adjust the size of the forearm sleeve. For example, FIG. 3 illustrates one type of adjustable attachment mechanism including strips with a part of a hook-and-loop fastening system, and FIG. 12 illustrates another type of adjustable attachment mechanism in which strips are combine with a cable system.

An operation of a sleeve will now be described with reference to the various figures. For explanatory purposes, the operation will be described with respect to fitting the sleeve 10 onto a right forearm, and in FIGS. 1, 2, 10, and 11, a ventral side of the right forearm is depicted.

In one aspect, the cuff 14 and the adjustable attachment mechanism of the sheath 16 are either not secured or are loosely secured. For example, portions 56A-C or portions 72A, 72B, and 56C may be not secured, or loosely secured to surface 54. The tubular body 12 is slid past a hand and onto a wrist and forearm, as depicted in FIGS. 2 and 11. As previously described, the pull tab 68 might be used to grip and pull the tubular body 12. The wrist and/or forearm may or may not have already been taped or wrapped prior to donning the sleeve 10 or 110. At this point, the tubular body 12 provides an initial amount of compression and support to the forearm and wrist. In addition, the tubular body 12 might be positioned on the forearm such that certain segments or parts of the sleeve are aligned with targeted areas of the forearm and wrist. For example, one or more less elastic segments 32 of the tubular body 12 might be aligned with an ulna region or a humerus region, whereas one or more elastic segments 30 might be aligned with regions of the forearm and wrist that have softer tissue. In addition, the adjustable attachment mechanism of the sheath 16 might be positioned on the ventral side of the forearm.

In a further aspect, after the tubular body 12 is pulled onto the forearm, the cuff 14 and the adjustable attachment mechanism of the sheath 16 can be used to provide additional support and compression to certain regions of the wrist and forearm. For example, the strip of textile segments of the cuff 14 can be wrapped clockwise (FIGS. 2 and 11), and the attachment end 40 can be secured to another portion of the cuff (e.g., 37). In addition, the elastic segment 38 of the cuff 14 allows the cuff 14 to be stretched while wrapping for additional compression and support.

In addition to the cuff 14, the sheath 16 can also be tightened to further enhance and customize the compression and support of the sleeve 10. In one aspect, the adjustment straps 56A, 56B, and 56C (FIGS. 1 and 2) or 72A, 72B, and 56C (FIGS. 10 and 11) can be pulled and secured onto the outer surface 54, thereby pulling the edges 44 and 46 towards one another and providing additional compression and support. In addition, specific zones of the sheath can be targeted independently of one another to provide more compression or less compression in a particular area because the sheath includes independent attachment straps.

As previously indicated, the sleeve 10 or 110 may be donned on a wrist and forearm that may or may not have already been taped or wrapped with an elastomeric strip that may or may not have an adhesive applied thereto. In instances in which the wrist and forearm have been taped or wrapped, the combination of the sleeve with the tape or wrap may provide certain results. For example, portions of the sleeve 10 or 110 may stretch less when the wrist and forearm have been pre-taped or pre-wrapped. In addition, this support system may help to induce a reflex (e.g., spring effect) within the wrist and forearm when engaging in certain motions or events that include throwing (or some other wrist action). Tape alone (without a sleeve according to the present technology) may move, spin, or otherwise adjust as a person engages in a particular activity as a result of stretching, loosening, sweat, dirt, and the like. But a sleeve in accordance with the present invention can be adjusted on-the-fly and as needed to achieve a particular degree of support and compression.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

The invention claimed is:

1. A forearm sleeve comprising:
an elastic tubular body having a first end and a second end and having an inward-facing surface and an outward-facing surface,
wherein the elastic tubular body includes a tubular wall comprised of a plurality of textile pieces coupled to one another;
wherein the plurality of textile pieces includes at least a first type of material and a second type of material; and
wherein the first type of material has an elasticity that is greater than the second type of material;
a cuff attached near the first end to the outward-facing surface, the cuff comprising a strip of one or more textile elements that includes an attachment end attached to the outward-facing surface and a releasably-attachable end that releasably attaches to at least one of another portion of the strip and the outward-facing surface; and
an adjustable forearm sheath that at least partially encases the elastic tubular body near the second end and that adjustably fastens around the elastic tubular body to adjust a size of the forearm sleeve.

2. The forearm sleeve of claim 1, wherein the elastic tubular body includes a first tubular segment that extends from the first end to a central region between the first end and the second end, and wherein the first tubular segment is comprised of a material having an amount of elasticity greater than the second type of material.

3. The forearm sleeve of claim 2, wherein the elastic tubular body includes a second tubular segment that extends from the second end to a central region between the second end and the first end, and wherein at least a portion of the second tubular segment is comprised of the second type of material having the lower amount of elasticity.

4. The forearm sleeve of claim 1 further comprising, an elongated rib element that axially extends along the elastic tubular body.

5. The forearm sleeve of claim 1, wherein the adjustable forearm sheath includes a sheet of textile that is less elastic than the elastic tubular body.

6. The forearm sleeve of claim 5,
wherein the sheet of textile includes a first edge and a second edge that extend radially around the elastic tubular body, the first edge positioned near the second end of the elastic tubular body and the second end positioned near the cuff;
wherein the sheet of textile material includes a third edge and a fourth edge that extend axially relative to the elastic tubular body and that couple the first edge to the second edge; and
wherein the first, second, third, and fourth edges comprise a perimeter boundary of a sheath body, which includes an internal surface facing towards the elastic tubular body and an external surface.

7. The forearm sleeve of claim 6, wherein the adjustable forearm sheath further comprises an adjustable attachment mechanism that releasably attaches at different positions to the external surface to adjust the size of the forearm sleeve.

8. The forearm sleeve of claim 7, wherein the adjustable attachment mechanism includes one or more hook-and-loop strips that extend from the sheath body near the third edge and that mate with a corresponding part of a hook-and-loop fastening system on the external surface.

9. The forearm sleeve of claim 7, wherein the adjustable attachment mechanism includes a cable that is attached at a first end to the sheath body, that slidably extends through a first eyelet and a second eyelet near the third edge, and that is attached at a second end to the sheath body, and wherein the adjustable mechanism includes another hook-and-loop strip attached to the cable along a portion of the cable extending between the first eyelet and the second eyelet, the other hook-and-loop strip mating with a corresponding part of a hook-and-loop fastening system on the external surface.

10. The forearm sleeve of claim 1, wherein the second end of the elastic tubular body includes a pull tab that is fixedly coupled to the second end and that includes an amount of elasticity that is less than the elastic tubular body.

11. The forearm sleeve of claim 1, wherein a segment of the elastic tubular body that extends from the first end to the second end is comprised of the second type of material.

12. A forearm sleeve comprising:
an elastic tubular body having a first end and a second end and having an inward-facing surface and an outward-facing surface;
a cuff attached near the first end to the outward-facing surface, the cuff comprising a strip of one or more textile elements that includes an attachment end attached to the outward-facing surface and a releasably-attachable end that releasably attaches to at least one of another portion of the strip and the outward-facing surface,
wherein the strip of one or more textile elements includes a first strip segment comprised of a first type of material and a second strip segment comprised of a second type of material, which is more elastic than the first type of material,
wherein the first strip segment extends from the attachment end to a central portion of the strip positioned between the attachment end and the releasably-attachable end, and
wherein the second strip segment extends from the first strip segment at the central portion of the strip to a hook-and-loop-fastener segment at the releasably-attachable end; and
an adjustable forearm sheath that at least partially encases the elastic tubular body near the second end and that adjustably fastens around the elastic tubular body to adjust a size of the forearm sleeve, the adjustable forearm sheath including:
  a sheet of textile that is less elastic than the elastic tubular body and that comprises a first edge, a second edge, a third edge, and a fourth edge, the first edge and the second edge extending radially around the elastic tubular body, the first edge positioned near the second end of the elastic tubular body and the second end positioned near the cuff,
    wherein the third edge and the fourth edge extend axially relative to the elastic tubular body, and
    wherein the first, second, third, and fourth edges comprise a perimeter boundary of a sheath body, which includes an internal surface facing towards the elastic tubular body and an external surface; and
  one or more adjustable attachment mechanisms, each of which releasably attaches to the sheet of textile at different positions to adjust an amount of compression on the elastic tubular body.

13. The forearm sleeve of claim 12, wherein the one or more adjustable attachment mechanism include a strap having a first part of a hook-and-loop fastening system that attaches to an outward-facing surface of the sheet of textile.

14. The forearm sleeve of claim 12, wherein the one or more adjustable attachment mechanism include a plurality of straps having a first part of a hook-and-loop fastening system that attaches to an outward-facing surface of the sheet of textile.

* * * * *